United States Patent [19]
Zandberg

[11] 4,228,341
[45] Oct. 14, 1980

[54] MECHANICAL CONTROL SYSTEM PARTICULARLY USEFUL FOR DIRECTING A LASER BEAM

[75] Inventor: Yoel Zandberg, Givataim, Israel

[73] Assignee: Laser Industries Ltd., Tel Aviv, Israel

[21] Appl. No.: 968,632

[22] Filed: Dec. 12, 1978

[51] Int. Cl.³ .............................................. B23K 27/00
[52] U.S. Cl. ......................... 219/121 L; 219/121 LU; 219/121 LZ
[58] Field of Search ..................... 219/121 L, 121 LM; 128/303.1; 350/285

[56] References Cited
U.S. PATENT DOCUMENTS

| | | | |
|---|---|---|---|
| 3,417,754 | 12/1968 | Smart | 219/121 L |
| 3,571,555 | 3/1971 | Townes et al. | 219/121 L |
| 3,720,213 | 3/1973 | Hobart et al. | 219/121 L |
| 4,110,009 | 8/1978 | Bunch | 350/292 |
| 4,126,136 | 11/1978 | Auth et al. | 128/303.1 |

*Primary Examiner*—C. L. Albritton
*Attorney, Agent, or Firm*—Benjamin J. Barish

[57] ABSTRACT

A mechanical control system for moving a controlled device in response to the movement of a universally movable control member, comprises a first ball mounted for universal movement in a first socket; a second ball mounted for universal movement in a second socket, and having one side facing one side of the first ball; the control member being coupled to the opposite side of the first ball; the controlled device being coupled to the opposite side of the second ball; and a connecting stem having a third ball at one end received in a third socket formed in said one side of the first ball, the opposite end of the stem being fixed to said one side of the second ball. The invention is described particularly for controlling a laser beam in accordance with the movement of a joy stick.

11 Claims, 6 Drawing Figures

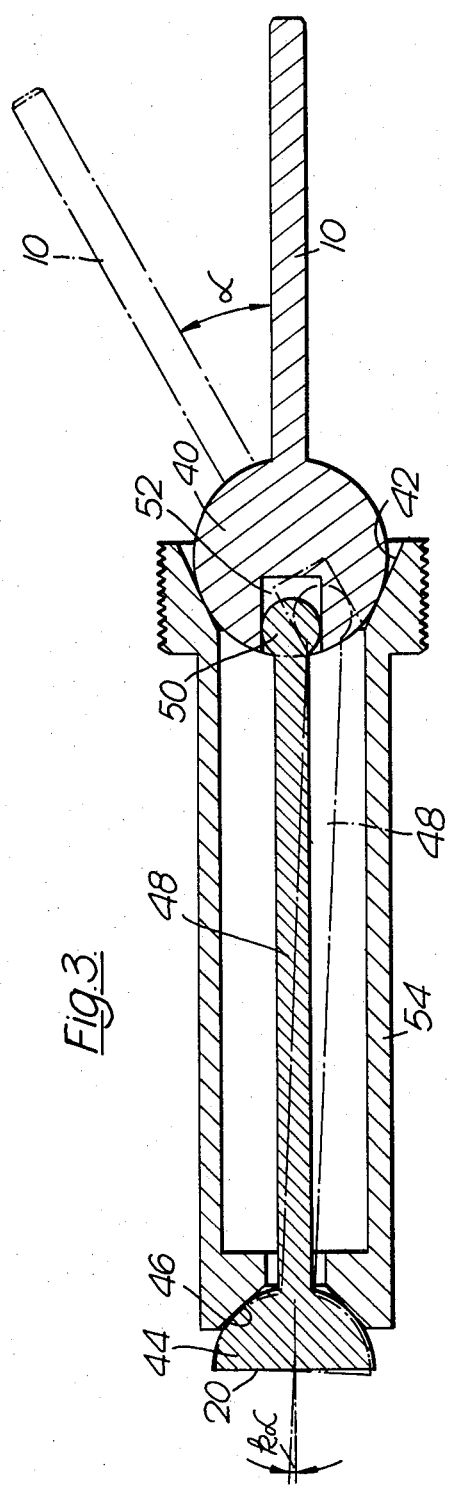
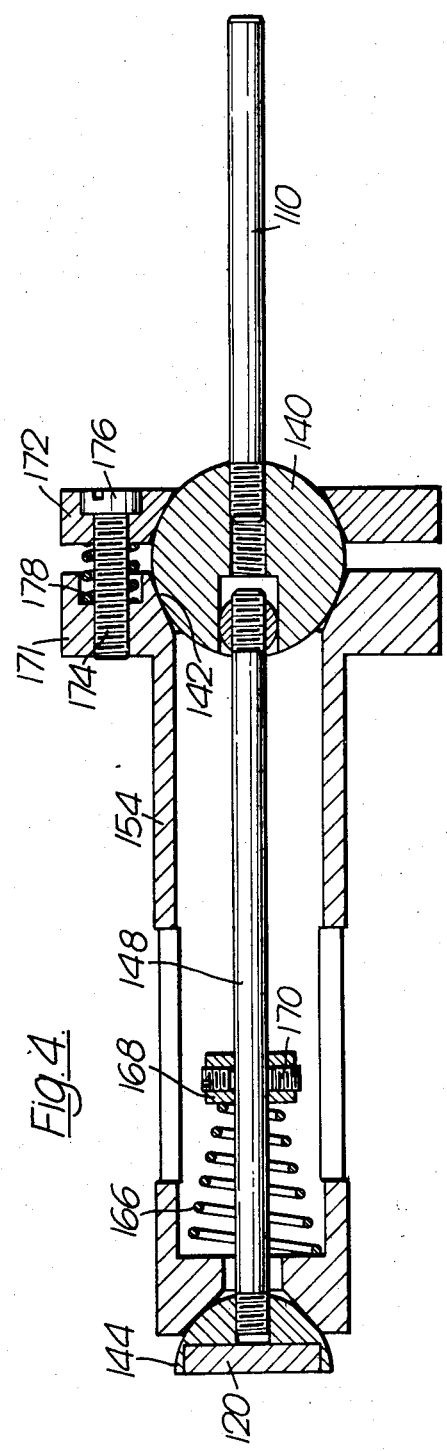

MECHANICAL CONTROL SYSTEM PARTICULARLY USEFUL FOR DIRECTING A LASER BEAM

BACKGROUND OF THE INVENTION

The present invention relates to a universal mechanical control system for moving a controlled device in response to the movement of a universally movable control rod. The invention is particularly applicable for controlling a laser beam surgical scalpel in accordance with the movement of a manipulatable joy stick and is therefore described below with respect to this application.

Laser beam surgical scalpels are increasingly being used for performing delicate surgical operations. A known type of such scalpels includes a microscope to permit viewing by the surgeon of the working area, and an optical control unit including a control rod, commonly called a joy stick, manipulatable by the surgeon for directing the laser beam with respect to the working area. Critical factors in the successful use of such scalpels for performing delicate surgery are the ease and precision by which the laser beam may be manipulated by the surgeon by using the joy stick. Various types of mechanical and electrical control systems have been proposed or are now in use for this purpose, but the known systems are generally of complicated, bulky, and expensive construction and/or are not entirely satisfactory with respect to the ease and precision by which they may be conveniently manipulated by the surgeon during the performance of a delicate surgical procedure.

An object of the present invention is to provide a simple, inexpensive and easily-operated mechanical control system for moving a controlled device in response to the movement of a universally movable control member. Another object of the invention is to provide a laser beam surgical scalpel with the above mechanical control system for manipulating the laser beam with respect to the working area in response to the manipulations of a joy stick.

SUMMARY OF THE INVENTION

According to one aspect of the present invention, there is provided a mechanical control system for moving a control device in response to the movement of a universally movable control member, comprising: a first ball mounted for universal movement in a first socket; a second ball mounted for universal movement in a second socket, and having one side facing one side of the first ball; the control member being coupled to the opposite side of the first ball; the controlled device being coupled to the opposite side of the second ball; and a connecting stem having a third ball at one end received in a third socket formed in said one side of the first ball, the opposite end of the stem being fixed to said one side of the second ball.

Two preferred embodiments of the invention are described below, in both of which the first socket includes an arrangement for varying the ease of movement of the first ball and the control member coupled thereto.

According to another aspect of the invention, there is provided a laser beam surgical scalpel comprising a microscope for viewing the working area, a laser beam generator for generating a laser beam, and an optical control unit in the path of the laser beam generated by the generator for directing the laser beam with respect to the working area, the latter optical control unit including a mechanical control system as set forth above for moving a reflector in the path of the laser beam in response to the movement of a joy stick manipulatable by the surgeon.

Further features and advantages of the invention will be apparent from the description below.

BRIEF DESCRIPTION OF THE DRAWINGS

The invention is herein described, by way of example only, with reference to the accompanying drawings, wherein:

FIG. 1a diagrammatically illustrates a portion of the surgical scalpel along lines A—A of FIG. 1.

FIG. 3 diagrammatically illustrates the operation of the optical control unit of FIG. 2; and FIG. 4 is a longitudinal sectional view illustrating a second form of mechanical control system that may be used in the optical control unit of FIGS. 1 and 2.

DESCRIPTION OF PREFERRED EMBODIMENTS

Figure 1:
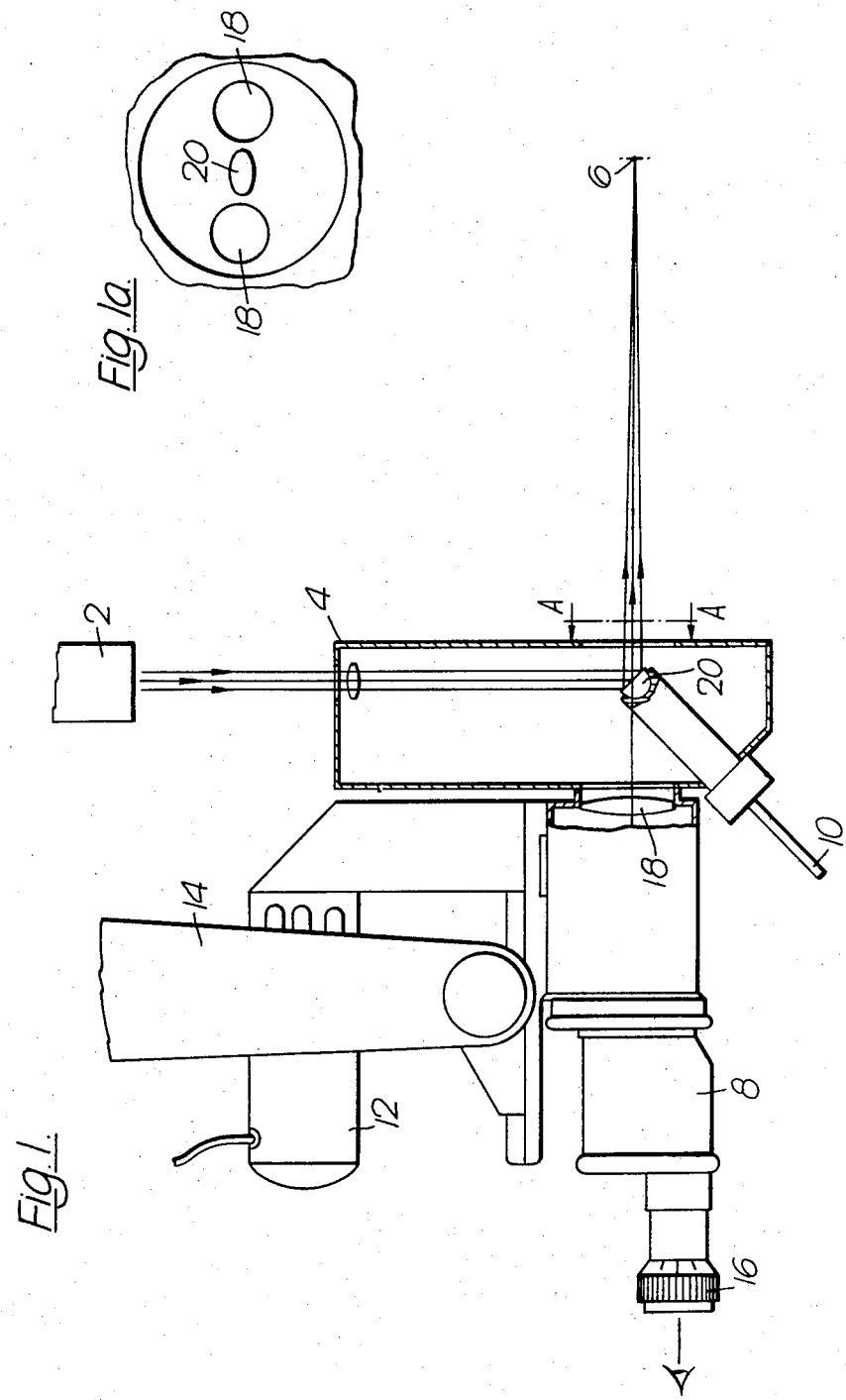
FIG. 1 is a diagram illustrating a laser beam surgical scalpel constructed in accordance with the present invention.

The laser beam surgical scalpel illustrated in FIG. 1 comprises a generator, generally designated 2, for generating a laser beam (actually two beams, namely a working beam and a guiding beam as described below); an optical control unit, generally designated 4, for directing the laser beam to a working area 6: and a microscope, generally designated 8, permitting the surgeon to view the working area 6 and to manipulate the laser beam with respect thereto by manipulating a joy stick 10 carried by the optical control unit 4. The working area is illuminated by a light source 12 attached to the microscope 8, to which is also attached the optical control unit 4. All the foregoing units are supported by an arm 14, which may be part of an articulated supporting structure known in laser surgical scalpels.

As also known in such scalpels, the microscope 8 includes a pair of eyepieces 16 and a pair of objective lenses 18 aligned with the optical unit 4 on opposite sides of a reflector 20 (See FIG. 1a), which reflector is moved by manipulating the joy stick 10 in order to direct the laser beam from generator 2 with respect to the working area 6.

Figure 2:
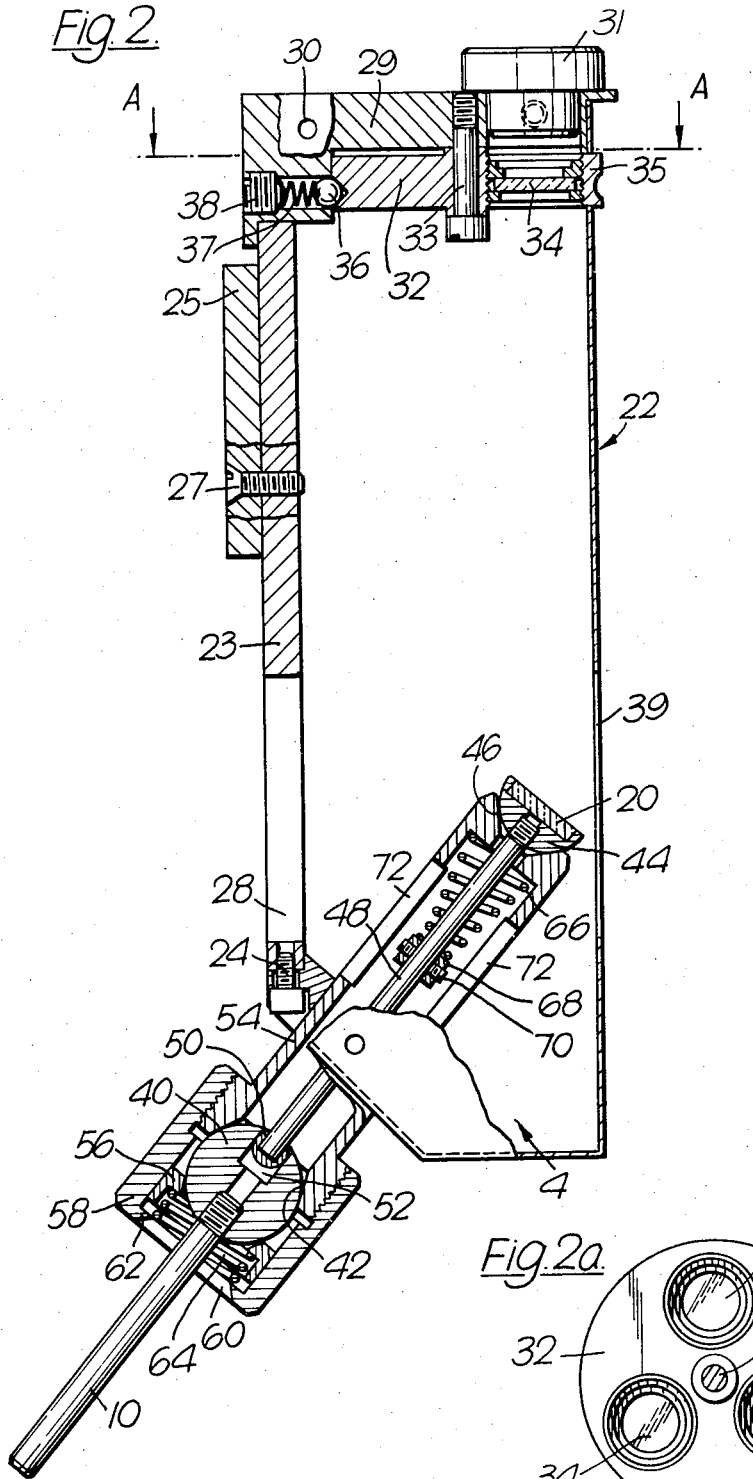
FIG. 2 is an enlarged longitudinal sectional view of the optical control unit in the surgical scalpel of FIG. 1.
Figure 2A:
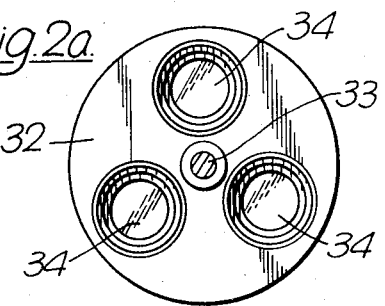
FIG. 2a is a transverse sectional view along lines A—A of FIG. 2.

The optical control unit 4 is more particularly illustrated in FIGS. 2 and 2a. Thus, it includes a housing 22 having a wall 23 removably attached to the housing by fasteners 24. The housing is attachable to the microscope 8 by means of a mounting bar 25 secured to wall 23 by fasteners 27. Wall 23 is formed with an opening 28 aligned with the objective lenses 18 (FIG. 1) of the microscope 8, when the optical control unit 4 is attached to it.

The upper end of the housing 22 is provided with a cover 29 pivotably mounted by a hinge 30 and having a window 31 aligned with the laser beam from generator 2. A lens holder 32 is rotatably mounted to cover 29 by means of a pin 33, holder 32 including three lenses 34 (See FIG. 2a) which are selectively positionable in alignment with window 31. Holder 32 may be manually rotated for selectively aligning one of the lenses 34 by means of a knurled rim 35 formed on the holder and projecting exteriorly of the housing. The lens holder 32 is retained in its preselected position by ball 36 seatable in one of three detents formed on the outer rim of the lens holder, the ball being urged by a spring 37 interposed between it and an adjustable set-screw 38. Reflector 20 is disposed within housing 22 in alignment with window 31 and the selected lens 34 so as to be impinged by the laser beam from generator 2, and to reflect same out of an opening 39 in the housing 22 towards the working area 6 in response to the manipulations of the joy stick 10 by the surgeon.

Reflector 20 and the manipulatable joy stick 10 are included in a mechanical control system which further includes a first ball 40 mounted for universal movement in a first socket 42, a second ball 44 mounted for universal movement in a second socket 46, and a connecting stem 48 having a third ball 50 at one end pivotable in a third socket 52 formed in ball 40, the opposite end of the stem being fixed to the second ball 44 by being threaded within an opening therein. The joy stick 10 is fixed to the first ball 40 by also being threaded in an opening formed in that ball opposite to its socket 52 facing ball 44. Reflector 20 is fixed to ball 44 on the side thereof opposite to that facing ball 40. For this purpose, ball 44 is actually semi-spherical, and the reflector is in the form of a separate member secured to its flat face; alternatively, it may merely constitute the polished flat face of that ball.

The two sockets 42, 46 are formed in the opposite ends of a cylinder 54 having openings the sides of which are rounded or conical and are engaged by the respective balls 40 and 44. Ball 40 is pressed against the conical opening in the end face of cylinder 54 by means of an annular bearing member 56 which is retained by collar 58 threaded onto the annular end of cylinder 54, the latter being thickened for this purpose. Collar 58 is formed with a central opening 60 through which the joy stick 10 passes, opening 60 being circumscribed by an inwardly extending flange 62. A coil spring 64 is interposed between bearing member 56 and flange 62 and urges the bearing member against ball 40.

It will be appreciated that by threading collar 58 more or less on the end of cylinder 54, the force applied by spring 64 against bearing member 56 bearing against ball 40 may be adjusted for varying the ease of movement of ball 40 within its socket 42, and thereby the ease of movement of the joy stick 10 by the surgeon.

The second ball 44 at the opposite end of cylinder 54 is retained within its socket 46 by a second coil spring 66 interposed between the inner end face of cylinder 54 defining the socket, and a ring 68 constituting a stop fixed to stem 48. The ease of moving ball 44 within its socket 46 may be adjusted by selectively fixing stop 68 along stem 48 to vary the compression of spring 66. For this purpose, stop 68 is attached to stem 48 by a set screw 70, and in addition, cylinder 54 is formed with one or more openings 72 to provide access to stop 68 for adjusting it along stem 48.

FIG. 3 illustrates how the manipulation of joy stick 10 coupled to ball 40 moves ball 44, and thereby its reflector 20, to manipulate the laser beam impinging that reflector. Thus, displacing joy stick 10 by the angle "$\alpha$" to its broken-line position, will cause socket 52 in ball 40 to be displaced in the opposite direction, whereby connecting stem 48, whose ball 50 is received within socket 52, is displaced to its broken-line position, such that ball 44, attached to the opposite end of stem 48, is displaced in the same direction as joy stick 10 by an angle "$\kappa\alpha$", which is a function of angle "$\alpha$" displacement of the joy stick 10.

It is not necessary that "$\alpha$" be a constant; That is, it is not necessary that there be a linear relationship between the displacement of reflector 20 with respect to the displacement of joy stick 10. The surgeon, when moving joy stick 10, is not making measured movement of the joy stick so as to require precise corresponding measured movements of the reflector 20, but rather is using the joy stick to manipulate the beam as he views it through the microscope eye pieces 16. Accordingly, the precision required is in precisely positioning the laser beam as the surgeon views it while manipulating the joy stick 10, and not in the precision between measured movements of the joy stick 10 producing corresponding movements of the reflector 20. The mechanical control system described above nicely meets the requirements of the surgeon in manipulating the laser beam since the device enables the beam to be conveniently and precisely manipulated in all directions by the use of the joy stick 10, and the "feel" of movement of the joy stick may be easily preset by presetting the degree of compression of the two springs 64 and 66 in the manner described above.

As mentioned above, unit 2 actually directs two laser beams to the optical unit 4, one being a working beam (e.g., a $CO_2$ laser beam) which performs the surgical operation, and the other being a guiding beam (e.g., a He-Ne laser beam) which is used for guiding or targeting purposes. In using the surgical scalpel, the operator first energizes the guiding (He-Ne) laser beam which is manipulated by joy stick 10 onto the working area 6, and when this beam is precisely positioned on the desired spot, the working ($CO_2$) laser beam is then energized to effect the surgical operation. The use of a guiding laser beam with a working laser beam is already known and does not form a part of the present invention.

FIG. 4 illustrates a variation that may be used in the construction of the mechanical control system for moving the reflector, therein designated 120, in response to the manipulation of the joy stick, therein designated 110. The construction of this control unit is basically the same as described above, and as particularly illustrated in FIG. 2, except for the arrangement for varying the ease of movement of the first ball, designated 140, within the first socket 142. For this purpose, cylinder 154 whose apertured end face forms a part of socket 142, is provided with an annular flange 171. The bearing member is in the form of a ring 172 of the same dimensions as flange 171 and includes a tapered or conical inner surface engageable with ball 140. A plurality of pins 174 (only one of which is illustrated in FIG. 4) is threaded into annular flange 171 and freely passes through openings in ring 172, the opposite end of each pin being formed with an enlarged head 176 abutting against the end of the ring. A coil spring 178 is disposed around each pin 174 between flange 171 and ring 172. It will thus be seen that threading pins 174 more or less into flange 170 will vary the compression of springs 178, and, thereby, the force applied by ring 172 against ball 140 and the ease of manipulation of joy stick 110.

The ease of manipulation of ball 144 carrying the reflector 120 may be varied in the same manner described with respect to FIG. 2, namely by the use of a fastener 170 to preset ring 168 along stem 148 to thereby vary the contraction of spring 166.

While the invention has been described with respect to two preferred embodiments, it will be appreciated that many variations, modifications and other applications of the invention may be made.

What is claimed is:

1. A mechanical control system for moving a controlled device in response to the movement of a universally movable control member, comprising: a first ball mounted for universal movement in a first socket; a second ball mounted for universal movement in a second socket, and having one side facing one side of the first ball; the control member being coupled to the opposite side of the first ball; the controlled device being coupled to the opposite side of the second ball; and a connecting stem having a third ball at one end received in a third socket formed in said one side of the first ball, the opposite end of the stem being fixed to said one side of the second ball.

2. A system according to claim 1, wherein said first socket includes a spring, a bearing member urged by said spring against said first ball, and adjustable means for adjusting the force applied by said spring against said bearing member for varying the ease of movement of the first ball and of the control member coupled thereto.

3. A system according to claim 2, wherein said adjustable means comprises a collar threaded onto an annular portion of said first socket, said spring being interposed between said collar and the bearing member and effective to vary the force applied by the latter against said first ball in accordance with the extent of threading of the collar onto said annular portion of the first socket.

4. A system according to claim 2, wherein said adjustable means comprises a threaded pin threaded into an annular portion of said first socket and freely passing through said bearing member, said pin including an enlarged head engaging the side of said bearing member opposite to said first socket, said spring being interposed between said annular portion of the first socket and said bearing member and effective to vary the force applied by the latter against said first ball in accordance with the extent of threading of the pin into said annular portion of the first socket.

5. A system according to claim 1, wherein said connecting stem passes through an opening formed in said second socket and includes a spring urging same in the direction to press said second ball against said second socket.

6. A system according to claim 5, wherein said spring is interposed between said second socket and a stop carried by said connecting stem.

7. A system according to claim 1, for controlling a beam of electromagnetic radiations, wherein the control member is a manipulatable joy stick, and the controlled device is a reflector reflecting said radiations in accordance with the manipulations of the joy stick.

8. A system according to claim 7, wherein said reflector is one for reflecting a laser beam.

9. A laser beam surgical scalpel, comprising: a microscope for viewing a working area; a laser beam generator for generating the laser beam; and an optical control unit in the path of the laser beam from the generator to the working area including a mechanical control system in accordance with claim 1, in which the control member is a manipulatable joy stick, and the controlled device is a reflector for reflecting said laser beam in accordance with the manipulations of the joy stick.

10. A laser beam surgical scalpel according to claim 9, wherein said microscope includes a pair of eyepieces and a pair of objective lenses aligned with said optical control unit on opposite sides of said reflector.

11. A laser beam surgical scalpel according to claim 9, wherein said microscope is mounted on said optical control unit for movement therewith.

* * * * *